(12) United States Patent
Gu et al.

(10) Patent No.: US 10,517,562 B2
(45) Date of Patent: Dec. 31, 2019

(54) MOBILE RADIOGRAPHY SYSTEM AND METHOD FOR ALIGNING MOBILE RADIOGRAPHY SYSTEM

(71) Applicant: GENERAL ELECTRIC COMPANY, Schenectady, NY (US)

(72) Inventors: Jiajun Gu, Shanghai (CN); Hao Lai, Niskayuna, NY (US); Li Tao, Shanghai (CN); Hao Xu, Shanghai (CN); Kun Tao, Shanghai (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 203 days.

(21) Appl. No.: 15/719,079

(22) Filed: Sep. 28, 2017

(65) Prior Publication Data
US 2018/0092619 A1 Apr. 5, 2018

(30) Foreign Application Priority Data

Sep. 30, 2016 (CN) .......................... 2016 1 0875664

(51) Int. Cl.
*A61B 6/00* (2006.01)
(52) U.S. Cl.
CPC ............ *A61B 6/587* (2013.01); *A61B 6/4064* (2013.01); *A61B 6/4291* (2013.01); *A61B 6/4405* (2013.01); *A61B 6/547* (2013.01)
(58) Field of Classification Search
CPC .................................................... A61B 6/587
See application file for complete search history.

(56) References Cited

U.S. PATENT DOCUMENTS

| | | | |
|---|---|---|---|
| 6,702,459 B2 | 3/2004 | Barnes et al. | |
| 7,744,279 B2 | 6/2010 | Heath et al. | |
| 7,798,710 B1 | 9/2010 | Barnes et al. | |
| 8,696,200 B2 | 4/2014 | Mohr | |
| 8,827,554 B2 | 9/2014 | Lalena et al. | |
| 9,055,886 B1 | 6/2015 | Garretson et al. | |
| 9,179,886 B2 | 11/2015 | Stagnitto et al. | |
| 2014/0241504 A1 | 8/2014 | Lundstrom et al. | |
| 2015/0223764 A1* | 8/2015 | Kwak | A61B 6/4429 378/63 |
| 2016/0073973 A1* | 3/2016 | Sheridan | A61B 6/035 378/205 |

(Continued)

OTHER PUBLICATIONS

Cho, Hyo-Min, et al.; "Imaging Characteristics of Mobile Digital Radiographic System", International Conference on Control, Automation and Systems, pp. 2411-2414, Oct. 17-20, 2007.

(Continued)

*Primary Examiner* — Yara B Green
(74) *Attorney, Agent, or Firm* — Fletcher Yoder, P.C.

(57) ABSTRACT

A mobile radiography system is disclosed, which includes a radiation source for radiating a plurality of beams; a detector for detecting the plurality of beams from the radiation source; a controller for determining an angular difference between the radiation source and the detector; and a positioning device mounted with the radiation source for recognizing a position of the detector relative to the radiation source based on the angular difference between the radiation source and the detector to align the radiation source to the detector. A method of aligning a mobile radiography system including a radiation source and a detector is also disclosed.

10 Claims, 7 Drawing Sheets

(56) References Cited

U.S. PATENT DOCUMENTS

2016/0166230 A1* 6/2016 Kim ................. A61B 6/587
378/205
2019/0021690 A1* 1/2019 Munier .............. A61B 6/587

OTHER PUBLICATIONS

Gauntt, David M., et al.; "An Automatic and Accurate X-ray Tube Focal Spot/grid Alignment System for Mobile Radiography: System Description and Alignment Accuracy", PubMed, Vloume 37, Issue 12, pp. 6402-6410, Dec. 2010.
"Carestream DRX-Revolution", Carestream Health, http://www.carestream.in/drx-revolution.html, 2016.

* cited by examiner

MOBILE RADIOGRAPHY SYSTEM AND METHOD FOR ALIGNING MOBILE RADIOGRAPHY SYSTEM

BACKGROUND

This disclosure relates generally to a radiography imaging technology, and more particularly to a mobile radiography system and aligning method thereof.

Mobile digital radiography (DR) systems are widely used in hospitals. The image quality of mobile DR is usually not as good as fixed DR systems. One major reason is that when using a mobile system, the operator has to manually adjust both x-ray tube and detector. While for fixed system, the detector's position is fixed in most cases. The operator only adjusts the position of x-ray tube, which travels along two or three orthogonal axis. Since the tube and detector are well aligned for fixed systems, anti-scatter grids are used to improve contrast-to-noise ratio of x-ray image. For mobile DR systems, artifacts caused by anti-scatter grids can be found in the x-ray image if the x-ray tube and detector are not well aligned.

In order to align the radiation source and the detector, the radiation source should be aligned to the center of the detector with predetermined distance and the center beam of the radiation source should be perpendicular to the detector. It will be a challenge to align the radiation source and the detector to meet all these three requirements.

There have been a number of approaches to the problem of providing methods and tools to assist operator adjustment of the radiation source and detector. A U.S. Pat. No. 9,179,886 entitled "Alignment apparatus for x-ray imaging system" introduces a method for aligning a radiation source with a portable image receiver in a radiographic imaging system generates a magnetic field with a predetermined field pattern and with a time-varying vector direction at a predetermined frequency from an emitter apparatus that is coupled to the radiation source, wherein the generated magnetic field further comprises a synchronization signal. Sensed signals from the magnetic field are obtained from a sensing apparatus that is coupled to the image receiver, wherein the sensing apparatus comprises three or more sensor elements, wherein at least two of the sensor elements are arranged at different angles relative to each other and are disposed outside the imaging area of the image receiver. An output signal is indicative of an alignment adjustment according to the amplitude and phase of the obtained sensed signals relative to the synchronization signal. This method uses magnetic field technology to retrieve the relationship between a radiation source and a portable image receiver. However, the magnetic field can be easily interfered by the surrounding environment. This method further has drawback of low precision and high cost.

A U.S. Pat. No. 9,055,886 entitled "Automatic tool alignment in a backscatter x-ray scanning system" introduces technologies pertaining to backscatter x-ray scanning systems. This disclosure introduces an alignment method based on the x-ray image. The first x-ray image is captured and region of interest is selected from the image. The proposed system will automatically align the x-ray source and detector and retake a second x-ray image. The drawback of this method is that the patient has to take risks of being exposed with extra dose of X-rays, because second shot of X-ray is required.

Thus, it can be seen that there is a need for an apparatus that enables proper alignment of a radiation source relative to an image detector with optional anti-scatter grid for taking a radiation image.

BRIEF DESCRIPTION

In at least one embodiment, the present disclosure provides a mobile radiography system. The system comprises a radiation source for radiating a plurality of beams; a detector for detecting the plurality of beams from the radiation source; a controller for determining an angular difference between the radiation source and the detector; and a positioning device mounted with the radiation source for recognizing a position of the detector relative to the radiation source based on the angular difference between the radiation source and the detector to align the radiation source to the detector. The system comprises two orientation sensors mounted on the radiation source and the detector respectively for determining the angular difference between the radiation source and the detector. The detector comprises at least two spacedly apart markers with LED respectively. The positioning device comprises a camera.

In at least one embodiment, the present disclosure provides a method for aligning a mobile radiography system including a radiation source and a detector. The method for aligning a mobile radiography system including a radiation source and a detector comprises determining an angular difference between the radiation source and the detector; recognizing a position of the detector relative to the radiation source; aligning the radiation source and the detector based on the position of the detector and the angular difference between the radiation source and the detector, wherein recognizing the position of the detector comprises capturing an image of the detector. The method further comprises setting a priori model of the detector, producing a perspective transformation of the priori model of the detector based on the angular difference between the radiation source and the detector; comparing the perspective transformation with the position of the detector on the image captured by camera, and determining a center area of the detector. Wherein aligning the radiation source and the detector comprises aligning the center area of the detector with a center of a lightened area indicating the center of the radiation source.

The embodiments described herein provide alignment system and method for mobile DR user in clinics. With these embodiments, mobile DR operators can well align x-ray tube with detector according visual or vocal instructions they are given instead of aligning based on their experience or instinct. Well aligned detector and x-ray tube can help to reduce retake and improve workflow efficiency in clinics. With well aligned detector and x-ray tube, anti-scatter grid can be used to improve image quality with relative low dose.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Embodiments of the present disclosure will be described herein below with reference to the accompanying drawings. In the following description, well-known functions or constructions are not described in detail to avoid obscuring the disclosure in unnecessary detail.

Unless defined otherwise, technical and scientific terms used herein have the same meaning as is commonly understood by one of ordinary skill in the art to which this disclosure belongs. The terms "first", "second", "third" and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean either or all of the listed items. The use of "including," "comprising" or "having" and variations thereof herein are meant to encompass the items listed thereafter and equivalents thereof as well as additional items. In addition, the terms "connected" and "coupled" are not restricted to physical or mechanical connections or couplings, and can include electrical connections or couplings, whether direct or indirect.

Embodiments of this disclosure may be described herein in terms of functional components and various processing steps. It should be appreciated that such functional components may be realized by any number of hardware, software, and/or firmware components configured to perform the specific functions. For example, at least one embodiment may employ various integrated circuit components, e.g., memory elements, digital signal processing elements, logic elements, look-up tables, or the like, which may carry out a variety of functions of "controller" under the control of one or more microprocessors or other control devices. Moreover, the system described herein merely illustrates at least one embodiment.

Figure 1:
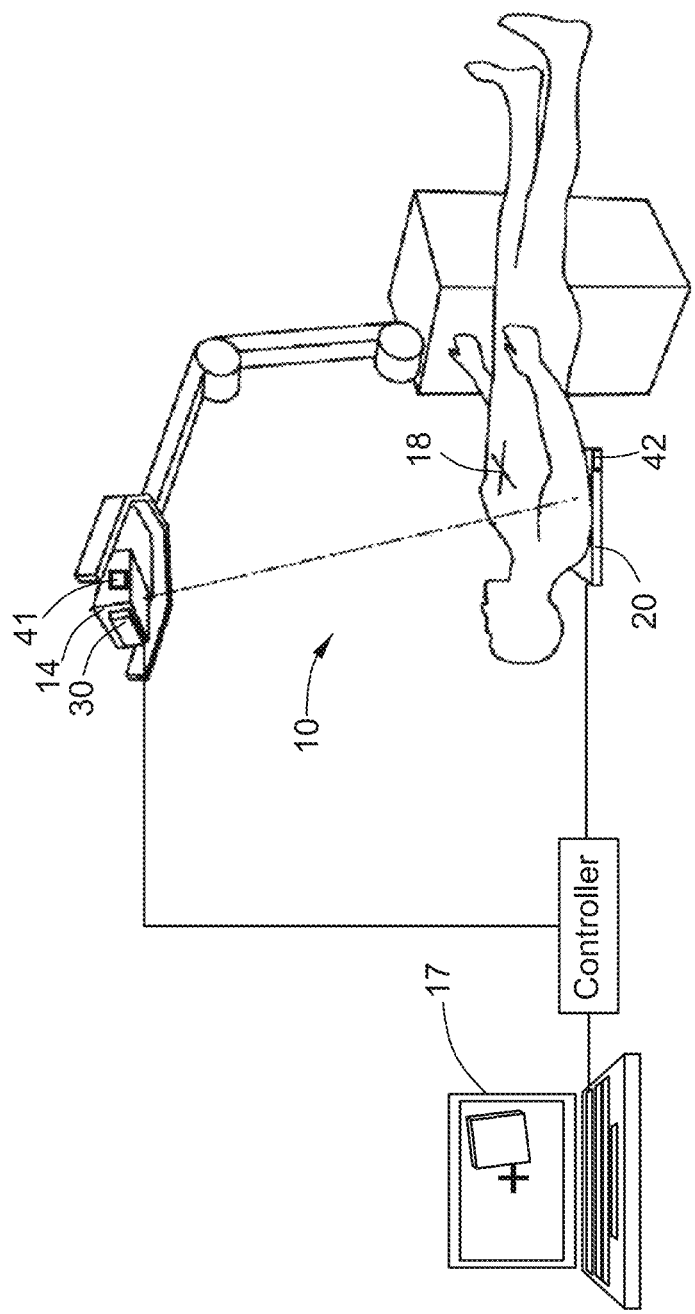
FIG. 1 is a perspective view of a mobile radiography system in accordance with at least one embodiment of the present disclosure.

FIG. 1 is a perspective view of a mobile radiography system 10 in accordance with at least one embodiment of the present disclosure. As shown in FIG. 1, the mobile radiography system 10, for example, a mobile x-ray imaging system may include a radiation source 14 and a detector 20.

The radiation source 14, in form of a tube, radiates a plurality of beams, such as X-ray beam or Gamma ray beam toward a detector 20. The detector 20 detects the plurality of beams that pass through an object 200 including multiple materials, such as a patient, from the radiation source 14. Detector 20 in form of a pad, has a photosimulable medium that records an image according to the beams emitted from the radiation source 14 to produce an electrical signal that represents the beams passing through the object 200. The patient can lie down in a horizontal position as shown in FIG. 1, and also can be at an oblique or even vertical angle, depending on the type of image that must be obtained.

In order to align the radiation source 14 and the detector 20, the central beam from the radiation source 14 that may also be a center axis of the radiation source tube is best to be substantially perpendicular to the surface of the detector 20.

The mobile radiography system 10 comprises a controller 16 for determining an angular difference between the radiation source 14 and the detector 20. The mobile radiography system 10 comprises two orientation sensors 41, 42 mounted on the radiation source 14 and the detector 20 respectively, so that the controller 16 can obtain orientation of the radiation source 14 and the detector 20 respectively, then subtract the orientation of the radiation source 14 by the orientation of the detector 20 or vice versa, and finally can determine angular difference between the radiation source 14 and the detector 20 according to the subtraction result. The orientation sensor can sense the angle between the radiation source or the detector and a reference. An initial value may be given to each of the orientation sensors with respective to a specific orientation of the radiation source or the detector. More specifically, each of the two orientation sensors 41, 42 comprises an inertial sensor in at least one embodiment of the present disclosure. Because the central beam emitted from the radiation source has fixed angular relationship with the surface of the radiation source, such as perpendicular to the surface of the radiation source, the orientation of the surface of the radiation source and the detector can be aligned by adjusting either the radiation source or the detector according to the angular difference 15 between the radiation source 14 and the detector 20 determined in real-time by the controller 16 to make sure the central beam is substantially perpendicular to the detector.

Figure 2:
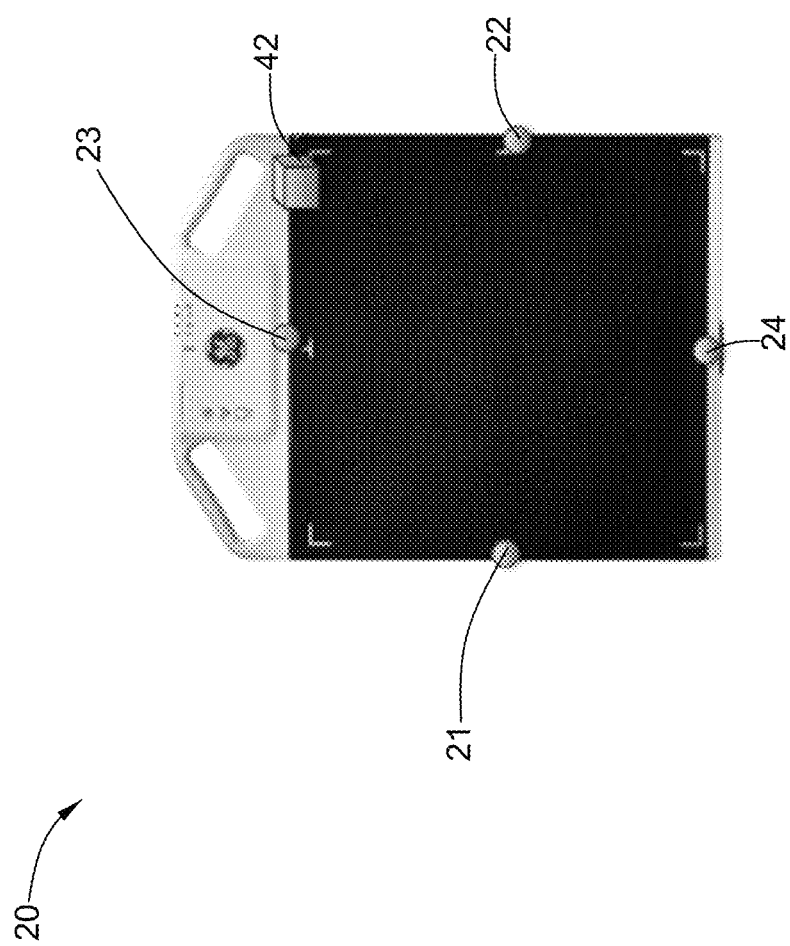
FIG. 2 is a perspective view of a detector of the mobile radiography system in accordance with at least one embodiment of the present disclosure.

The mobile radiography system 10 comprises a positioning device 30 mounted with the radiation source 14 for recognizing a position of the detector 20 relative to the radiation source 14 based on the angular difference between the radiation source and the detector to align the radiation source 14 to the detector. Preferably, the positioning device comprises visual sensor, more specifically, a camera, or an invisible light sensor, which will be introduced afterwards. In at least one embodiment of the present disclosure, the position of the detector is captured through the image of the detector recorded by the camera. In at least one other embodiment of the present disclosure, the detector comprises at least two spacedly apart markers 21,22 detectable to the positioning device 30. Refer to FIG. 2 of the drawings, four markers 21,22,23,24 are arranged on edge of the detector, to be exactly, on center of four sides of the detector respectively, so that the position of the detector can be recognized by the visual sensor. In another example, the markers are provided on an extension element connected with the detector and extending outwardly from the detector, so that the all markers on the detector won't be blocked, even when the patient is too big. The extension element is connected with the detector by a shaft, and can be opened by or turned when it needs to be used to extend outwardly from the edge of the detector, so that the markers can be detected by the visual sensor and camera. The markers comprise a LED respectively. When LED emits visible light, a visual sensor or camera can be used to capture the LED markers.

When LED emits invisible light, an invisible light sensor can be used to identify the LED markers.

The position of the detector 20 relative to the radiation source 14 recognized by the visual sensor mounted with the radiation source 14 changes based on the angular difference between the radiation source 14 and the detector 20, because the position of the detector 20 recognized by the visual sensor is planar view of the detector and changes due to the orientations of the radiation source 14 and the detector 20 respectively. Therefore, a preferred position of the detector can be determined based on the image of the detector or the markers on the detector recognized by the positioning device and the angular difference between the radiation source and the detector, and then the detector can be adjusted to be aligned with the radiation source.

Figure 5:
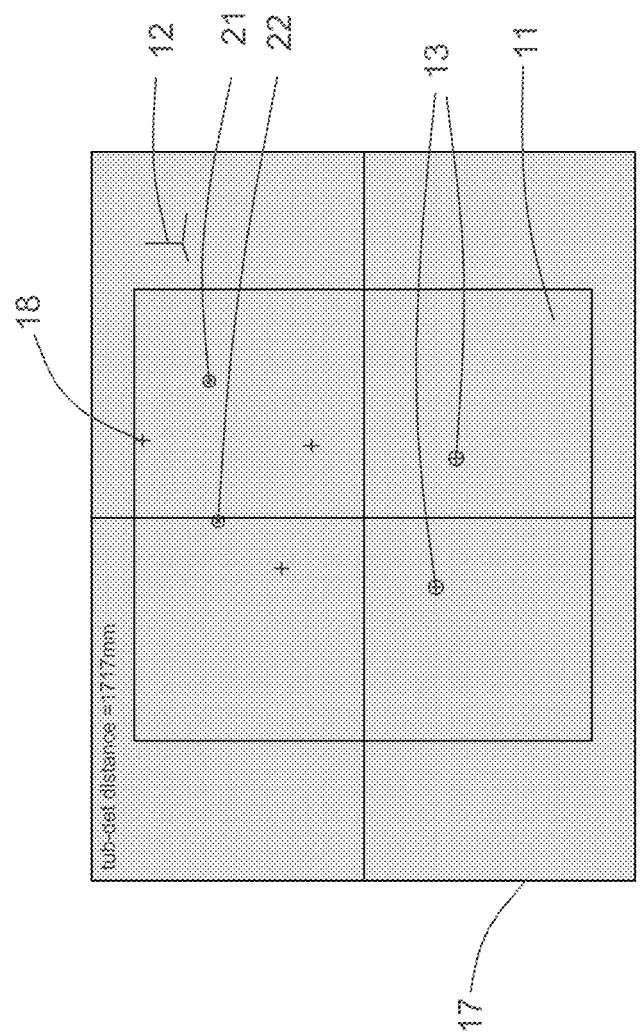
FIG. 5 is a display showing alignment status of a mobile radiography system in accordance with at least one embodiment of the present disclosure.

Referring to FIG. 5 of the drawings, the mobile radiography system 10 comprises a display 17 receiving data from the camera, the two inertial sensors, and the controller, on which the planar view of the detector 20 based on the angular difference calculated by the controller showing the position of the detector 20 relative to the radiation source 14 is displayed, and the angular difference of the radiation source and the detector is also displayed. On FIG. 5, the angular difference between the radiation source and the detector 12 is displayed. Therefore, an operator can adjust the radiation source or the detector to align the radiation source and the detector to a proper angular difference and relative position.

The positioning device 30 is mounted on the side of the radiation source in at least this embodiment, so that there will be an offset between the radiation source and the positioning device, because the position is captured by the positioning device not the radiation source. The offset between the radiation source and the positioning device is pre-calibrated, so that the planar view of the detector 20 relative to the radiation source 14 can be obtained and displayed on the display.

Figure 3:
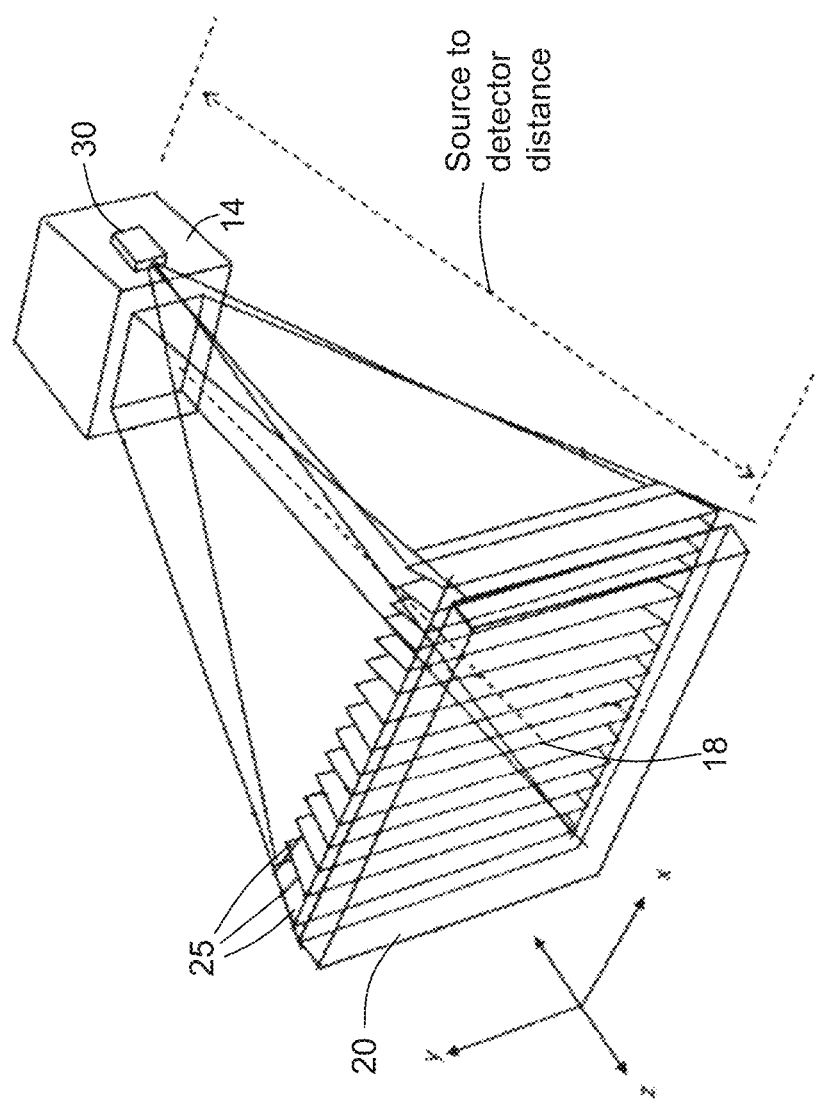
FIG. 3 is a perspective view of a mobile radiography system showing alignment of a radiation source and a detector in accordance with at least one embodiment of the present disclosure.

In some cases, as shown in FIG. 3 anti-scatter grids 25 is disposed on the detector to absorb scatter to get more clear radiography image. When the anti-scatter grids are used, the radiation source 14 needs to be aligned to a predetermined area of the detector, preferably a center area of the detector, and more specifically the center of the detector 18. The center of the detector cannot be captured directly by the camera, because it will be blocked by a patient to be scanned.

Figure 4:
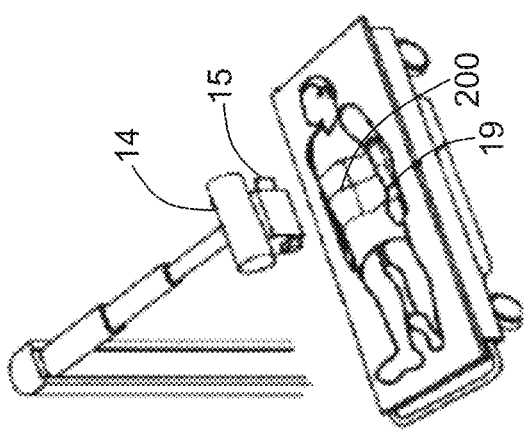
FIG. 4 is a perspective view of a mobile radiography system in accordance with at least one embodiment of the present disclosure.

Referring to FIG. 4 of the drawings, the mobile radiography system 10 comprises a light source 15 mounted on the side of and close to the radiation source 14. The light source 15 emits a light, such as white light, to the patient to indicate a field of interest 19 on a patient to be scanned. The light area has a cross thereon shown on the patient in FIG. 4. The center of the cross indicates a center of the radiation source to be aligned with a center of the detector.

In order to determine the center of the detector 18, the controller has a priori model of the detector and produces a perspective transformation of the priori model of the detector based on the angular difference between the radiation source and the detector. Compare the perspective transformation with the position of the detector obtained by the image of the markers on the detector or the image of the detector, so that the center of the detector can be determined.

The priori model reflects the data of the detector, containing the location of the markers and the center of the detector in at least one embodiment, or containing the length, and width of the detector in at least one other embodiment, or containing other data that can be used to achieve the same goal. The controller produces a perspective transformation of the priori model of the detector including the markers and the center area on the detector based on the angular difference between the radiation source and the detector, and maps the perspective transformation of the priori model of the detector onto the display. The controller also maps the position of the detector including the position of the markers captured by the visual sensor onto the display, which is a planar view. Compare the perspective transformation of the priori model of the detector including the markers and the center area with the position of the detector including the position of the markers captured by the visual sensor, so that the center of the detector can be determined by the controller and shown on the display. The center of the cross of the field of interest is also displayed on the display on FIG. 5. Move the detector or the radiation source to adjust the center of the detector on the display to align with the center of the cross of the field of interest, which is also displayed on the display on FIG. 5, to make sure the radiation source and the detector are well aligned.

Besides the center beam of the radiation source needs to be perpendicular to the detector and the radiation source needs to be aligned with the center of the detector, a third factor, which is the distance between the radiation source and the detector, needs to be a predetermined value so as to well align the radiation source and the detector.

In order to make sure the distance between the radiation source and the detector is the predetermined value, in at least one embodiment, the first distance between two markers on the detector captured by the positioning device is measured, then obtain the second distance between the two markers of the perspective transformation of the priori model of detector based on the angular difference between the radiation source and the detector, and compare the first distance with the second distance to get the distance between the radiation source and the detector. Because the longer is the distance between the radiation source and the detector, the shorter is the first distance between the at least two spacedly apart markers captured by the visual sensor with respective to the second distance between the two markers of the perspective transformation of the priori model of detector based on the angular difference between the radiation source and the detector.

Further referring to FIG. 5 of the drawings, the perspective transformation of two markers 13 the prior model of the detector is mapped on the display, so as to be compared with the position of the two markers 21, 22 of the detector captured by the camera, which is also mapped on the display. By comparison, the center is the detector is calculated and shown on the display. The operator can manually adjust the center of the detector with the center of the cross of white light, which is also mapped onto the display. The distance between the radiation source tube and the detector, shown as "tub-det distance" is also displayed.

The controller further comprises an instruction module that is capable of giving operator instructions to align the radiation source and the detector, such as vocal or visual instructions showing moving up, down, closer and adjusting orientation, etc. to make sure that the orientation of the radiation source is aligned to the orientation of the detector, the radiation source is aligned to the center of the detector, and the distance between the radiation source and the detector is predetermined value.

The operator can align the radiation source and the detector in two ways. In the first way, operator can first place the detector behind patient then move the radiation source tube towards the detector. When moving tube, visual or vocal instructions will be given to the operator to guide the tube's movement. In the other way, operator can first move tube toward patient and make sure x-ray will cover the entire region of interest with the help from white light installed on tube. Then operator can move detector and insert it behind the patient. During that, instructions will guide detector's movement letting the central x-ray from tube passing through its center. Finally, operator can refine tube's position and orientation according to instructions so that the x-ray can be perpendicular to the detector.

Figure 6:
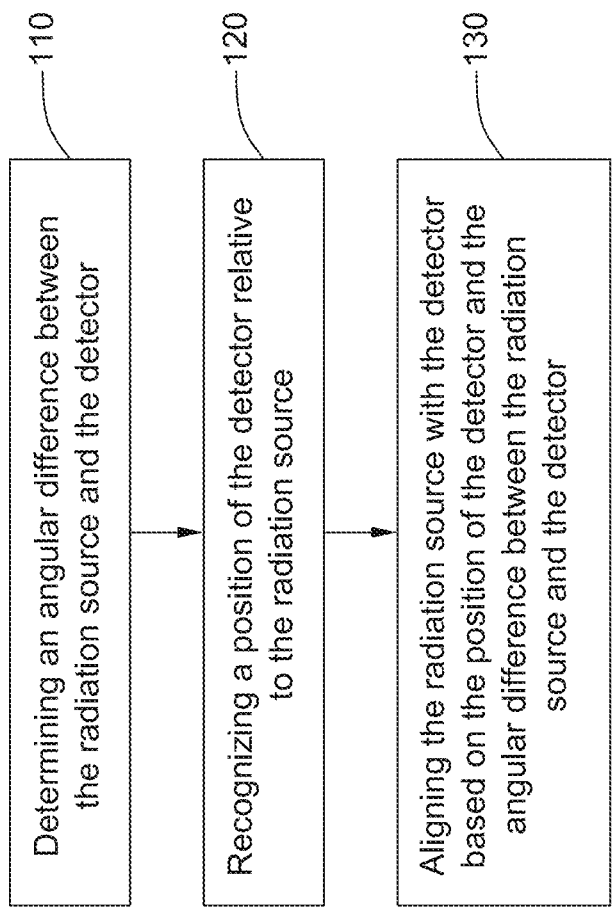
FIG. 6 illustrates steps how to align a mobile radiography system in accordance with at least one embodiment of the present disclosure.
Figure 7:
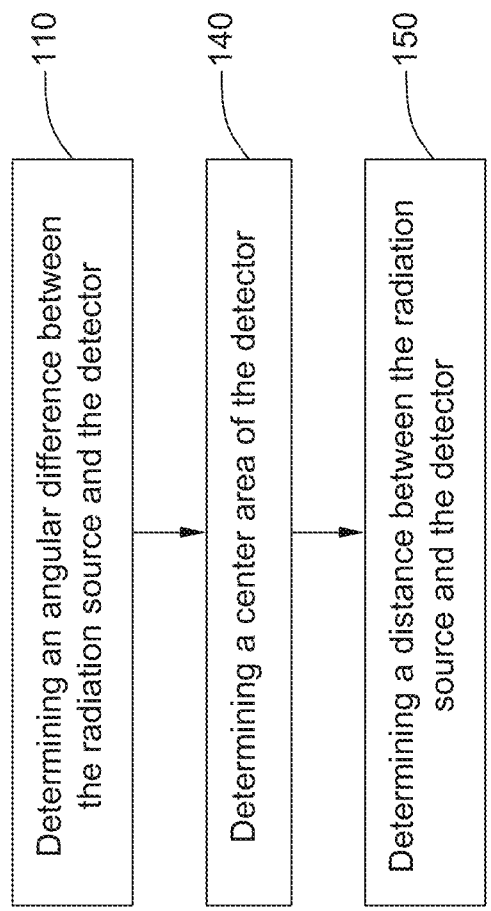
FIG. 7 illustrates three factors to be determined to align a mobile radiography system in accordance with at least one embodiment of the present disclosure.

Referring to FIGS. 6 and 7 of the drawings, the present disclosure also provides a method for aligning a mobile radiography system including a radiation source and a detector. FIG. 6 illustrates steps on how to align a mobile radiography system in accordance with at least one embodiment of the present disclosure, wherein a method for aligning a mobile radiography system including a radiation source and a detector comprises: step 110 of determining an angular difference between the radiation source and the detector by a controller; step 120 of recognizing a position of the detector relative to the radiation source; and step 130 of aligning the radiation source and the detector based on the position of the detector and the angular difference between the radiation source and the detector.

Determining an angular difference between the radiation source and the detector comprises determining an orientation of the radiation source and the detector respectively. The method provides two orientation sensors 41, 42 mounted on the radiation source 14 and the detector 20 respectively, obtains the orientation of the radiation source 14 and the detector 20 respectively, then subtracts the orientation of the radiation source 14 by the orientation of the detector 20 or vice versa, and the angular difference between the radiation source 14 and the detector 20 can be determined according to the subtraction result. The orientation sensor is a device that is capable of obtaining the angle between the radiation source or the detector and a reference. The method gives an initial value to each of the orientation sensors with respective to a specific orientation of the radiation source or the detector. More specifically, the two orientation sensors 41, 42 are two inertial sensors respectively in at least one embodiment of the present disclosure. Because the central beam emitted from the radiation is perpendicular to the surface of the radiation source, aligning the radiation source and the detector comprises adjusting either the radiation source or the detector according to the angular difference 15 between the radiation source 14 and the detector 20 determined in real-time by the controller 16 to make sure that the central beam is substantially perpendicular to the detector.

In at least one embodiment, recognizing the position of the detector comprises capturing an image of the detector; in at least one other embodiment, recognizing the position of the detector comprises capturing at least two spacedly apart markers of the detector. The position of the detector recognized by a positioning device is a planar image of the detector or the markers on the detector from the view of the positioning device, and is displayed on a display. Preferably, the positioning device comprises visual sensor, more specifically, a camera or an invisible light sensor, by which a planar image of the detector or the markers on the detector showing the position of the detector is captured, so that the radiation source is aligned with the detector according to the position of the detector in addition to the angular relationship of the radiation source and the detector.

Refer to FIG. 2 of the drawings, four markers 21,22,23,24 are arranged on edges of the detector, to be exactly on center of four sides of the detector respectively, so that the position of the detector can be recognized through the markers on the detector. The method comprises providing light source to the at least two spacedly apart markers respectively. Wherein capturing at least two spacedly apart markers comprises identifying lights from at least two spacedly apart markers of the detector respectively. When LED emits visible light, a visual sensor or camera can be used to capture the LED markers. When LED emits invisible light, an invisible light sensor can be used to identify the LED markers.

The position of the detector 20 relative to the radiation source 14 recognized by the visual sensor mounted with the radiation source 14 changes according to the angular difference between the radiation source 14 and the detector 20, because the position of the detector 20 recognized by the visual sensor is planar view of the detector and changes due to the orientation of the radiation source 14 and the detector 20. Therefore, a preferred area of the detector can be determined based on the image of the detector or the markers on the detector recognized by the positioning device and the angular difference between the radiation source and the detector, and then can be adjusted to be aligned with the radiation source.

In some cases, as shown in FIG. 3, anti-scatter grids 25 are disposed on the detector to absorb scatter to get more clear radiography image. When the anti-scatter grids are used, the radiation source needs to be aligned to a predetermined area of the detector, preferably a center area of the detector, and more specifically the center of the detector 18. The method of aligning a mobile radiography system comprises a step 140 of determining the center of the detector.

The method for aligning a mobile radiography system including a radiation source and a detector comprises setting a priori model of the detector, producing a perspective transformation of the priori model of the detector based on the angular difference between the radiation source and the detector; comparing the perspective transformation 13 containing data of the center area of the detector with the position of the detector shown on the display; and determining the center area of the detector.

Priori model of the detector is real data from the detector, in at least one embodiment which includes the length, width and etc. of the detector. In at least this embodiment, the center of the detector can be calculated from the length and width of the detector, or given in the priori model. In at least one embodiment priori model of the detector includes location of the markers on the detector and center of the detector. Therefore, by comparison, the center of the detector is determined, and the radiation source can be aligned with the center area of the detector.

The method for aligning a mobile radiography system including a radiation source and a detector comprises providing a lightened area on the object 200 from a light source 15 mounted on and close to the side of the radiation source 14. The light source 15 emit a light to the patient to indicate a field of interest to be scanned. The light area has a cross thereon indicating a center of the radiation source to be aligned with a center of the detector. In this case, aligning the radiation source and the detector comprises aligning the center area of the detector with a center of a lightened area indicating the center of the radiation source.

Further, the method comprises mapping the perspective transformation of the priori model of the detector into each image of camera, and displaying perspective transformation of the priori model of the detector and the image of camera on a display, on which the perspective transformation of the priori model of the detector is compared with the position of the detector, so that the center of the detector 18 is determined. The method also maps the lightening area 11 with a cross thereon indicating the center of the radiation source onto the display, and also show the center of the detector 18 on the display, so that the operator can adjust the radiation source or the detector to align the center of the detector with the center of the cross.

The method comprises mapping the angular difference of the radiation source and the detector onto the display to make sure that the central beam of the radiation source is perpendicular to the detector.

FIG. 7 illustrates three factors to be determined to align a mobile radiography system, which are the angular difference between the radiation source and the detector, the center area of the detector, and the distance between the radiation source and the detector. The first and second factors are illustrated above.

The method further comprises step 150 of determining a distance between the radiation source and the detector. The method comprises obtaining a first distance between the at least two spacedly apart markers captured by the positioning device, comparing the second distance between the at least two spacedly apart markers of perspective transformation of a priori model of the detector based on the angular difference between the radiation source and the detector, and determining a distance between the radiation source and the detector. For example, calculating the proportion of the first distance between the at least two spacedly apart markers captured by the positioning device to the second distance of the at least two spacedly apart markers of a perspective transformation of a priori model of the detector based on the angular difference between the radiation source and the detector, and then the distance between the radiation source and the detector can be known. Because the longer is the distance between the radiation source and the detector, the shorter is the first distance between the at least two spacedly apart markers captured by the positioning device with respective to the second distance between the two markers of the perspective transformation of the priori model of detector based on the angular difference between the radiation source and the detector.

The method for aligning a mobile radiography system including a radiation source and a detector comprises displaying the distance between the radiation source and the detector to make sure that the radiation source and the detector is well aligned.

The method for aligning a mobile radiography system including a radiation source and a detector comprises providing instructions for aligning the radiation source and the detector, such as vocal or visual instructions showing moving up, down, closer, etc. to make sure that the orientation of the radiation source is aligned to the orientation of the detector, the radiation source is aligned to the center of the detector, and the distance between the radiation source and the detector is predetermined value.

With the method of the present disclosure, the radiation source and the detector is aligned according to the angular difference between the radiation source and the detector, location of the center of the detector, and the distance between the radiation source and the detector. After the radiation source and the detector is aligned, an image can be taken for a patient by the mobile radiography system.

While the disclosure has been illustrated and described in certain embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A mobile radiography system, comprising:
   a radiation source for radiating a plurality of beams;
   a detector for detecting the plurality of beams from the radiation source;
   a controller for determining an angular difference between the radiation source and the detector;
   a positioning device mounted with the radiation source for recognizing a position of the detector relative to the radiation source based on the angular difference between the radiation source and the detector to align the radiation source to the detector;
   two orientation sensors mounted on the radiation source and the detector respectively for determining the angular difference between the radiation source and the detector.

2. The system of claim 1, wherein the detector comprises at least two spaced apart markers detectable to the positioning device.

3. The system of claim 2, wherein the at least two spaced apart markers comprise a LED respectively.

4. The system of claim 1, wherein the positioning device comprises a visual sensor for capturing an image of the detector.

5. A method for aligning a mobile radiography system including a radiation source and a detector, comprising:
   determining an angular difference between the radiation source and the detector; recognizing a position of the detector relative to the radiation source based on the angular difference between the radiation source and the detector;
   setting a priori model of the detector, producing a perspective transformation of the priori model of the detector based on the angular difference between the radiation source and the detector;
   comparing the perspective transformation with the position of the detector; and determining a center area of the detector; and
   aligning the radiation source and the detector based on the position of the detector and the angular difference between the radiation source and the detector.

6. The method of claim 5, wherein recognizing the position of the detector comprises capturing an image of the detector.

7. The method of claim 5, wherein aligning the radiation source and the detector comprises aligning the center area of the detector with a center of a lightened area indicating the center of the radiation source.

8. The method of claim 5, wherein determining the angular difference comprises determining an orientation of the radiation source and the detector respectively.

9. The method of claim 5, comprising displaying the position of the detector relative to the radiation source based on the angular difference between the radiation source and the detector.

10. A method for aligning a mobile radiography system including a radiation source and a detector, comprising:
    determining an angular difference between the radiation source and the detector; recognizing a position of the detector relative to the radiation source based on the angular difference between the radiation source and the detector;

recognizing the position of the detector comprises capturing at least two spaced apart markers of the detector;
obtaining a first distance between the at least two spaced apart markers captured by the positioning device, comparing the first distance with a second distance of the at least two spaced apart markers of a perspective transformation of a priori model of the detector based on the angular difference between the radiation source and the detector, determining a distance between the radiation source and the detector; and
aligning the radiation source and the detector based on the position of the detector and the angular difference between the radiation source and the detector.

* * * * *